United States Patent
Axelsen

(10) Patent No.: US 9,855,357 B2
(45) Date of Patent: Jan. 2, 2018

(54) RAPID SURFACE DISINFECTION METHOD AND APPARATUS

(71) Applicant: THE TRUSTEES OF THE UNIVERSITY OF PENNSYLVANIA, Philadelphia, PA (US)

(72) Inventor: Paul H. Axelsen, Wayne, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 717 days.

(21) Appl. No.: 14/197,711

(22) Filed: Mar. 5, 2014

(65) Prior Publication Data
US 2014/0186211 A1  Jul. 3, 2014

Related U.S. Application Data

(63) Continuation of application No. PCT/US2012/055517, filed on Sep. 14, 2012.
(Continued)

(51) Int. Cl.
*A61L 2/18* (2006.01)
*C11D 3/48* (2006.01)
(Continued)

(52) U.S. Cl.
CPC .............. *A61L 2/18* (2013.01); *A01N 59/00* (2013.01); *A61L 2/0088* (2013.01); *C11D 3/48* (2013.01); *C11D 7/02* (2013.01); *C11D 17/0043* (2013.01)

(58) Field of Classification Search
CPC ........ A61L 2/0088; A61L 2/0094; A61L 2/18; A61L 2/20; A61L 2/22; A61L 2/24;
(Continued)

(56) References Cited

U.S. PATENT DOCUMENTS 7,892,198 B2   2/2011  Stenzler
2005/0036949 A1  2/2005  Tucker et al.
(Continued)

OTHER PUBLICATIONS

Ghaffari et al., "A direct nitric oxide gas delivery system for bacterial and mammalian cell cultures," Nitric Oxide 12:129-140 (2005).
(Continued)

*Primary Examiner* — Timothy Cleveland
(74) *Attorney, Agent, or Firm* — Baker Botts L.L.P.

(57) ABSTRACT

A device for rapidly sanitizing a surface is described. The device has an enclosure having an opening adapted to insert a surface, and an interior; a liquid nitric oxide solution applicator; and an absorbent material. The liquid nitric oxide solution applicator is in fluid communication with the interior of the enclosure and is adapted to apply liquid nitric oxide solution onto the surface when the surface is positioned within the enclosure. A method of rapidly sanitizing a surface is described. The devices and methods provided herein may be implemented to sanitize the surface of any body part or item that may be placed within the device. An infectious agent on the surface may be killed; i.e., the surface is disinfected. Non-limiting applications of the devices and methods include preventing nosocomial infections or food contamination, sanitizing household items, and implementing sanitizing procedures to comply with FDA Good Manufacturing Practices.

13 Claims, 5 Drawing Sheets

Related U.S. Application Data

(60) Provisional application No. 61/535,683, filed on Sep. 16, 2011.

(51) Int. Cl.
  *C11D 7/02* (2006.01)
  *C11D 17/00* (2006.01)
  *A01N 59/00* (2006.01)
  *A61L 2/00* (2006.01)

(58) Field of Classification Search
  CPC .. A01N 59/00; C11D 7/02; C11D 3/48; C11D 17/0043
  See application file for complete search history.

(56) References Cited

U.S. PATENT DOCUMENTS

| | | |
|---|---|---|
| 2005/0137521 A1* | 6/2005 | Stenzler .............. A61M 1/0088 604/23 |
| 2005/0263387 A1 | 12/2005 | Thomas et al. |
| 2009/0299787 A1 | 12/2009 | Barnhill |
| 2010/0134296 A1 | 6/2010 | Hwang |

OTHER PUBLICATIONS

Gemci et al., "Chapter 7: Atomization, Spraying, and Nebulization," H.G. Merkus, G.M.H. Meesters (eds.), Production, Handling and Characterization of Particulate Materials, Particle Technology Series 25, pp. 201-256 (2016).

* cited by examiner

RAPID SURFACE DISINFECTION METHOD AND APPARATUS

This application is a continuation of International Application No. PCT/US12/055517 filed Sep. 14, 2012, which claims the benefit of U.S. provisional application No. 61/535,683, filed Sep. 16, 2011, the contents of each of which are incorporated herein by reference in their entireties, and to each of which priority is claimed.

FIELD

The disclosure herein relates to the field of sanitization.

BACKGROUND

Workplaces, hospitals, other healthcare facilities, schools, daycares, churches, manufacturing facilities, public places, and homes are all locations persons become susceptible to infection or may spread infection without sanitization of hands, other body parts or shared surfaces. Restaurants, kitchens and places where food is handled and served must sanitize surfaces and hands to prevent the spread of foodborne illnesses as well as prevent the spread of infection. Further, utensils that come into contact with hands and raw foods must be sanitized. Caregivers or others in hospitals or other healthcare facilities may reduce nosocomial infection rates through sanitization of hands. Sanitization issues apply in the veterinary context as well. Veterinarians must sanitize their hands between patients to prevent the spread of animal illness. Veterinary surgical equipment, instruments and clinic surfaces also need sanitization. Sanitization issues arise in complying with the Food and Drug Administration's Good Manufacturing Practices (GMPs). GMPs contain requirements and guidelines that apply to the manufacturing of food and drug products in a sanitary environment. GMPs require employee personal hygiene and hand sanitizing to prevent food product contamination and adulteration of pharmaceuticals and dietary supplements.

SUMMARY

In an aspect, the invention relates to a device for rapidly sanitizing a surface. The device includes an enclosure having an opening adapted to insert a surface to be treated and an interior. The device also includes a liquid nitric oxide solution applicator, and an absorbent material. The liquid nitric oxide solution applicator is in fluid communication with the interior of the enclosure and is adapted to apply liquid nitric oxide solution onto the surface to be treated when the surface is positioned within the enclosure.

In an aspect, the invention relates to a method of rapidly sanitizing a surface. The method includes providing a device for rapidly sanitizing a surface. The device has an enclosure having an opening adapted to insert a surface, and an interior. The device also has a liquid nitric oxide solution applicator, and an absorbent material. The liquid nitric oxide solution applicator is in fluid communication with the interior of the enclosure and a liquid nitric oxide solution source, and is adapted to apply the liquid nitric oxide solution onto a surface. The method also includes inserting a surface to be treated into the device, and applying the liquid nitric oxide solution to the surface to be treated.

In an aspect, the invention relates to a method of rapidly sanitizing a surface. The method includes inserting a surface to be treated into a device for rapidly sanitizing a surface. The device has an enclosure having an opening adapted to insert a surface, and an interior. The device also has a liquid nitric oxide solution applicator, and an absorbent material. The liquid nitric oxide solution applicator is in fluid communication with the interior of the enclosure and a liquid nitric oxide solution source, and is adapted to apply the liquid nitric oxide solution onto a surface. The method includes applying the liquid nitric oxide solution to the surface to be treated.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments, which are presently preferred. It is understood, however, that the invention is not limited to the precise arrangements and instrumentalities shown. In the drawings.

DETAILED DESCRIPTION OF EMBODIMENTS

Figure 1:
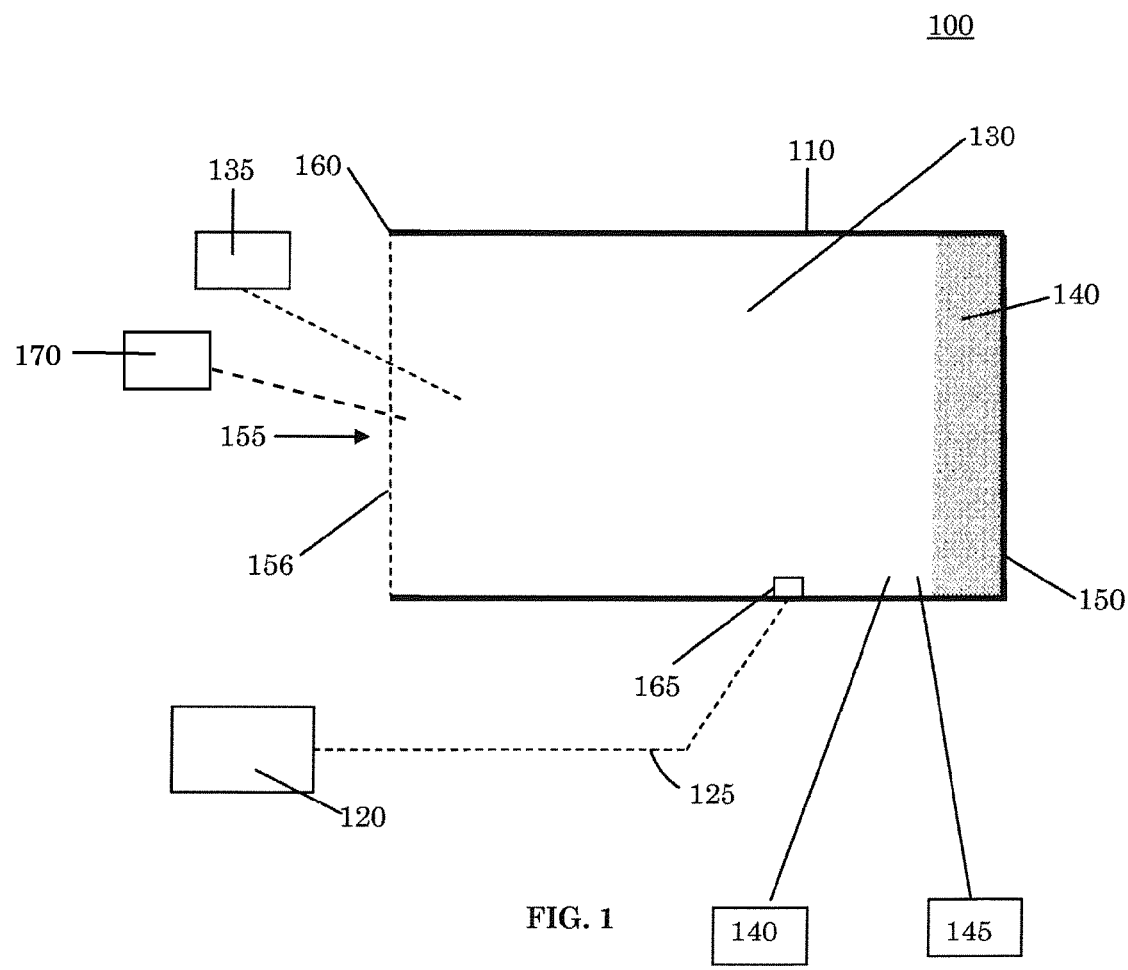
FIG. 1 illustrates a sanitizing device.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. The phrase at least one followed by a list of two or more items, such as A, B, or C, means any individual one of A, B or C as well as any combination thereof.

Embodiments herein include devices and methods for the rapid sanitization of surfaces. The devices and methods employ liquid nitric oxide as a sterilizing agent. Rapid and dry sanitization may be achieved when the liquid nitric oxide solution evaporates quickly from the surface. The devices and methods may be employed for the rapid decontamination of hands. The devices or methods may be but are not limited to use in workplaces, hospitals or other healthcare facilities (collectively, medical facilities), schools, daycares, churches, manufacturing facilities, public places, or homes. The devices or methods may be implemented to prevent the transmission of infectious agents. The devices, systems and methods may be used in addition to or as a replacement to handwashing.

The devices and methods may be used in combating infectious agents. An infectious agent may be a bacterial infectious agent. The bacterial infectious agent may be but is not limited to staphylococcus species; various gram negative species; anaerobic species; mycobacterial species; spore forms of various bacteria including but not limited to clostridia and bacillus species; filamentous species such as nocardia and actinomyces. The bacterial infectious agent may be subject to sanitizing or killing by the devices and methods herein without regard to whether any given species exhibits resistance to systemic antibiotics that might be used in humans and animals.

In an embodiment, a device for rapidly sanitizing a surface is provided. Preferably, sanitizing includes killing an infectious agent, i.e. the surface is disinfected. The device includes an enclosure having an opening adapted to insert a surface to be treated. The surface may be on an object. The object may be a body part, a hand, or an in-animate object. The body part or hand may be a human body part or hand or a non-nonhuman body part. The device includes a liquid nitric oxide solution applicator, and an absorbent material. The liquid nitric oxide solution applicator is in fluid communication with the interior of the enclosure and is adapted to apply liquid nitric oxide solution onto the surface. The absorbent material may absorb nitric oxide and reaction products with nitric oxide. A non-limiting example of an absorbent material is Purafil Chemisorbant Media, Item number CHM-BX from Advanced Filtration Concepts Inc., 7111 Telegraph Rd, Montebello, Calif. 90640. The device may also include a containment system for moving nitric oxide and reaction products with nitric oxide toward the absorbent material, or into a container or scrubber. The device may also include, and with reference to FIG. 1, a system 170 to deliver to and/or maintain an oxygen-free inert gas atmosphere in the interior of the enclosure. The oxygen-free inert gas atmosphere may include nitrogen, argon, carbon dioxide, another chemically unreactive gas, or combinations thereof.

In an embodiment a method of rapidly sanitizing a surface is provided to combat infectious agents. Preferably, the infectious agent is killed, i.e. the surface is disinfected. The surface may be on an object. The object may be a body part, a hand, or an in-animate object. The body part or hand may be a human body part or hand or a non-nonhuman body part. The method includes providing a device for rapidly sanitizing a surface. The device includes an enclosure having an opening adapted to insert the surface. The device includes a liquid nitric oxide solution applicator, and an absorbent material. The liquid nitric oxide solution applicator is in fluid communication with the interior of the enclosure and a liquid nitric oxide solution source, and is adapted to apply the liquid nitric oxide solution onto the surface. The absorbent material absorbs nitric oxide and reaction products with nitric oxide. The device may also include a containment system for moving nitric oxide and reaction products with nitric oxide toward the absorbent material, or into a container or scrubber. The device may also include a system to deliver to and/or maintain an oxygen-free inert gas atmosphere in the interior of the enclosure. The oxygen-free inert gas atmosphere may include nitrogen, argon, carbon dioxide, another chemically unreactive gas, or combinations thereof. The method also includes inserting a surface to be treated into the device, and applying the liquid nitric oxide solution to the surface to be treated. The liquid solvent may be water, various kinds of alcohol, other solvents, or a mixture of solvents. The method may be implemented by inserting a hand into the opening of the device, and applying the liquid nitric oxide solution to the surface by activating the liquid nitric oxide solution applicator. The method may also include activating the containment system. The method may also include delivering to and/or maintaining an oxygen-free inert gas atmosphere in the interior of the enclosure. The oxygen-free inert gas atmosphere may include nitrogen, argon, carbon dioxide, another chemically unreactive gas, or combinations thereof.

The method may be rapid and dry. In an embodiment, the method can be conducted for a 3 sec exposure, and afterwards the hands are dry with no residue. The method may be rapid and safe for use on skin, so that the method may be used not only for inanimate objects, but also to disinfect skin, which may be human skin.

The liquid nitric oxide solution may have various additives that stabilize and preserve the nitric oxide, or that synergize with nitric oxide to enhance its antimicrobial activity.

The surface may be any surface that can be inserted in the device. The surface may be a healthy intact portion of the human body, e.g. a hand or a foot, a material to be used or implanted in the human body, or any other surface with the potential to harbor bacteria. The surface may be part of or the entire surface of a personal item, a household item, a workplace item, a medical facility item, a school item, a daycare item, a church item, a manufacturing item, a food packaging item, a drug manufacturing item, a food or food ingredient, or a drug or drug component. Delivery of NO to the surface may be accomplished by nebulizing, atomizing, or vaporizing the nitric oxide solution. The vaporized solvent may be responsible for some of the effectiveness of the method, but neither the solvent alone, nor the NO alone, have a sufficiently complete or a sufficiently rapid ability to disinfect the surface.

Referring to FIG. 1, a non-limiting embodiment of the device for rapidly sanitizing a surface is illustrated. The device 100 includes an enclosure 110 and a liquid nitric oxide solution applicator 120 in fluid communication 125 with the interior 130 of the enclosure 110. The liquid nitric oxide solution applicator is adapted to apply liquid nitric oxide solution onto a surface to be treated. The fluid communication 125 may be any known in the art including but not limited to direct contact or a tube. The liquid nitric oxide solution applicator 120 may be located outside of, integral with or inside the enclosure 110. The enclosure 110 may contain absorbent material 140 configured to capture nitric oxide or products of reactions with nitric oxide. The device 100 may also include a containment system 135 for moving nitric oxide and reaction products with nitric oxide toward the absorbent material 140 and/or into at least one of a container 140 or a scrubber 145. The containment system 135 may include a fan configured to direct flow of liquid nitric oxide through the enclosure 110. The enclosure 110 may be any suitable shape including but not limited to cubical, spherical or cylindrical. The absorbent material 140 may be positioned in the enclosure 110 such that material flowing through the enclosure 110 impacts or passes through the absorbent material 140. The absorbent material 140 may be positioned at a first end 150 of the enclosure 110. The enclosure may have an opening 155. The opening 155 may be located at any suitable location on the enclosure such that a surface can be brought in proximity to the opening 155, or inserted through the opening 155 into the enclosure 110. The device 100 may include a moveable barrier 156. The moveable barrier 156 may be any type that allows insertion of a surface through the opening. The moveable barrier 156 may be flexible or retractable to reveal and allow a surface to access the opening 155. The moveable barrier may have a seam through which a surface may inserted through in order to access the opening 155. The opening 155 may be located at a second end 160 of the enclosure. The liquid nitric oxide solution applicator 120 may be inside or outside the enclosure 110. The liquid nitric oxide solution applicator 120 may be configured to deliver the liquid nitric oxide solution into the interior 130 of the enclosure 110. The liquid nitric oxide solution applicator 120 may include an atomizer, or high pressure release to dispense the liquid directly into the interior 130. The liquid nitric oxide solution applicator 120 may include a fluid conduit as a dispenser that could then be connected to one or more dispensers 165 configured that atomize, nebulize or otherwise release the liquid nitric oxide solution into the interior 130. The containment system 135 may be inside the enclosure 110 or otherwise configured to provide air circulation through the enclosure 110. The air circulation may be the means to direct NO or its reaction products to absorbent material 140.

A device for rapidly sanitizing a surface herein may include an actuator to facilitate dispensing of liquid nitric oxide solution from the liquid nitric oxide solution applicator. The actuator may be configured to actuate a valve that when open allows flow of the liquid nitric oxide solution. The actuator may be configured to actuate a pump operably connected to the liquid nitric oxide solution applicator 120. The pump may be a hand pump or an electromagnetic pump in the device and operably associate with the liquid nitric oxide solution applicator. A hand pump may be actuated by any known mechanical actuator. An electromagnetic pump may be actuated by an electromagnetic actuator. The actuation of the electromagnetic pump may be activated by a sensor. The sensor may detect the presence of a surface. The sensor may detect motion. The sensor may include a light sensor that detects when a light beam is broken by a surface. The sensor may include a graviometric scale that senses the weight of an object having a surface.

A device for rapidly sanitizing a surface herein may include a tracking element. The tracking element may require the user to swipe an identification card prior to using the device. The tracking element may track sanitization of a specific surface. The tracking element may track the sanitization of a specific worker. The tracking element may track the sanitization of a medical professional such as a physician, surgeon or nurse. The tracking element may include a biometric scan of the user. The tracking element may include a camera that takes a still picture of the user. The tracking element may include a video of the user. The tracking element may include an RFID tag to track a user or an object. The tracking element may include a record of the user or object being tracked. The tracking element may include a record of when or if a surface was sanitized with the device. In a non-restrictive embodiment, a tracking element may be added as an optional improvement to allow monitoring the identity and times of users. Monitoring the identity and times of users may be accomplished through RFID chips. Such monitoring may be used to document who has disinfected their hands, in what location and when, or prior to entering a particular room. Since a device may by configured to provide effective sanitization through its simple use, a positive indication of use of a device means compliance with a sanitization protocol. In contrast, soap and water sinks or alcohol dispensers including RFID chips may not provide the same information because a user could "log" usage of those methods without actually using them effectively; i.e. they could not distinguish between effective and ineffective compliance.

A device for rapidly sanitizing a surface herein may include one or more sensor. The one or more sensor may be used to sense an object or body part placed inside the device. The one or more sensor may detect a user's hands. The one or more sensor may detect which particular user utilized the system. The one or more sensor may record which of the user's hand was inserted in the system. The one or more sensor may track how much liquid nitric oxide solution is dispensed. The one or more sensor may actuate delivery of liquid nitric oxide from the device to the surface of the user or object upon sensing the presence of the surface. The delivery may be timed or metered based on a system parameter to insure sufficient liquid nitric oxide is available. The system parameter may be a single volume. The system parameter may be a time. The system parameter may be an amount of liquid nitric oxide solution per unit area of the surface inserted.

A device for rapidly sanitizing a surface herein may include one or more indicator. The one or more indicator may alert the user when sanitization begins. The one or more indicator may alert the user when the sanitizing is complete. The one or more indicator may alert the user through any known method including but not limited to a light or a sound.

In an embodiment, a method herein includes applying the liquid nitric oxide solution for one minute or less, 30 seconds or less, or 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 seconds or less. The application time may be a value in a range between any two integers from 1 to 30 seconds. Preferably, a method herein includes applying the liquid nitric oxide solution for 3 seconds.

Figure 4:
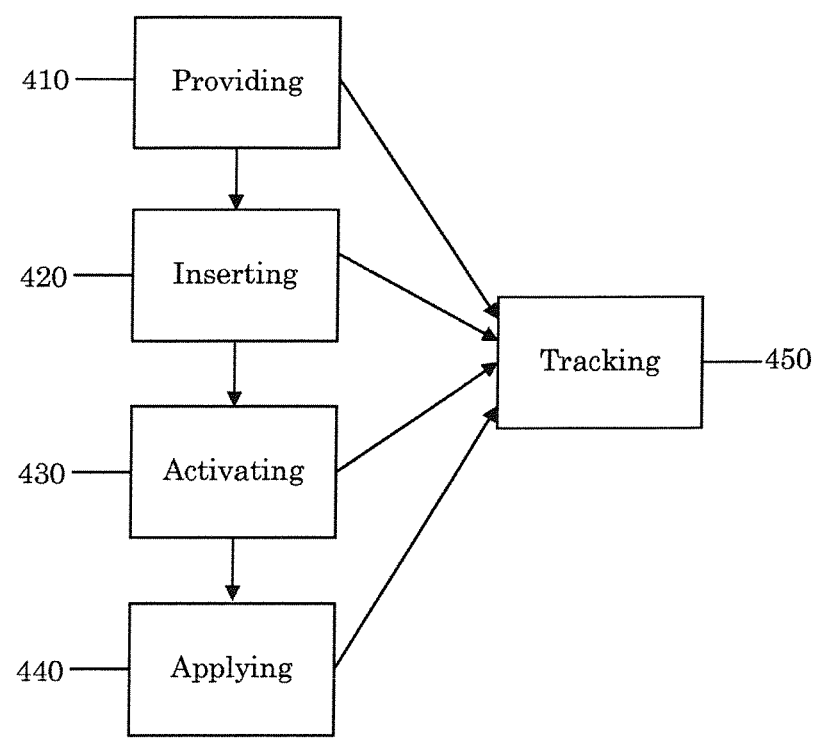
FIG. 4 illustrates a method of rapidly sanitizing a surface.

Referring to FIG. 4, a method 400 of rapidly sanitizing a surface is illustrated. Method 400 may include steps of providing 410, inserting 420, activating 430, applying 440, and tracking 450. Providing 410 may include providing any device for rapidly sanitizing a surface herein. Inserting 420 may include inserting a surface into the device for sanitizing the surface. Activating 430 may include activating any containment system herein. Applying 440 may include applying any liquid nitric oxide solution herein. Tracking 450 may include tracking a user's implementation of the device/method or the surface sanitation by any tracking means herein. Tracking 450 may occur at any one or more of steps 410, 420, 430 or 440. Tracking 450 may occur at all of steps 410, 420, 430 and 440.

Figure 5:
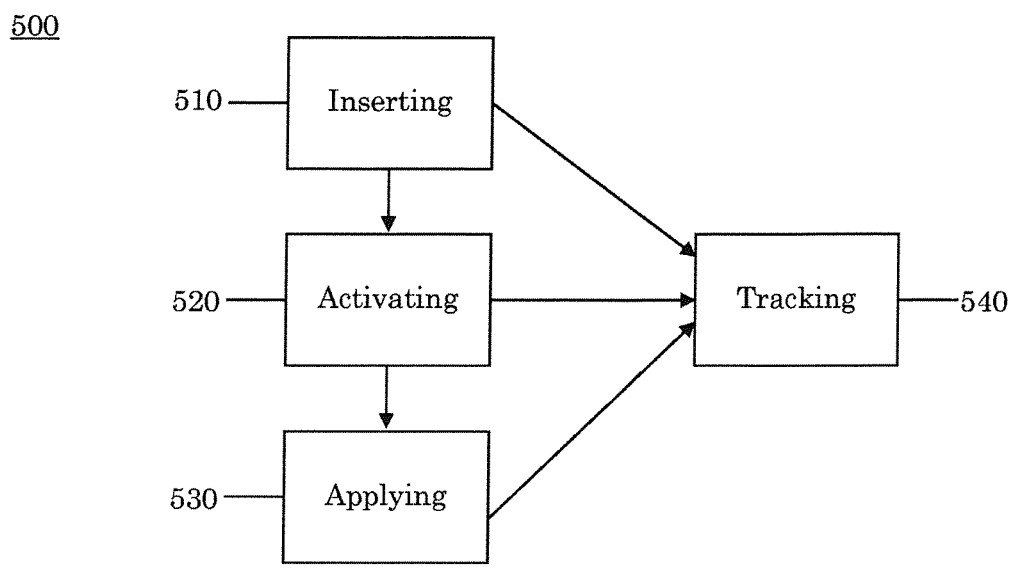
FIG. 5 illustrates a method of rapidly sanitizing a surface.

Referring to FIG. 5, method 500 of rapidly sanitizing a surface is illustrated. Method 500 may include steps of inserting 510, activating 520, applying 530 and tracking 540. Inserting 510 may include inserting a surface into a device for rapidly sanitizing a surface herein. Activating 520 may include activating any containment system herein. Applying 530 may include applying any liquid nitric oxide solution herein. Tracking 540 may include tracking a user's implementation of the device/method or the surface sanitation by any tracking means herein. Tracking 540 may occur at any one or more of steps 510, 520 or 530. Tracking 540 may occur at all of steps 510, 520 and 530.

A method provided by the present embodiments may include implementing the tracking elements of a device for rapidly sanitizing a surface herein. The method may include a computer implemented aspect. Instructions for the computer may be stored in a computer-readable medium and processor executable. Further embodiments include such instructions stored on a computer-readable medium. A method herein may include any method of tracking the user or surface to be treated known in the art, including self-reporting.

A system for rapidly sanitizing surfaces is provided in embodiments herein. The system may include at least one of a device for rapidly sanitizing a surface herein, tracking devices to implement tracking as described herein, or a computer as described herein or a network of more than one of said computers operably connected with at least one of the device, users, or surfaces.

A method provided by the present embodiments may be conducted to sanitize any type of device, object or surface that can be inserted into a device herein. The methods may be implemented using any of the devices contained herein. Non-limiting examples follow. A method herein may be implemented to prevent food contamination. Prevention may be accomplished by applying the nitric oxide solution to a worker's hands prior to the worker handling food, after the worker handles food, or prior to the worker serving food. A method herein may be implemented in drug, food or nutritional supplement manufacturing in order to comply with Food and Drug Administration Good Manufacturing Practices. Procedures to comply may include a worker sanitizing hands or implements. A method herein may be implemented to prevent nosocomial infection by applying the liquid nitric oxide solution to a caregiver's hands. The caregiver may be but is not limited to a physician, a surgeon, a nurse, a babysitter or a parent. The application of the liquid nitric oxide solution may occur prior to the caregiver's contact with the subject. The application of the liquid nitric oxide solution may occur after the caregiver's contact with the subject. The application of the liquid nitric oxide solution may occur after the caregiver's contact with a first subject and before contact with a second subject. Superficial cutaneous infections may be combated with a method herein. Such infections include but are not limited to those caused by bacteria or dematophytoses such as ringworm or athletes foot.

The liquid nitric oxide solution in embodiments herein includes nitric oxide and a liquid solvent. The concentration of nitric oxide dissolved in the liquid solvent may represent the equilibrium solubility limit of NO in that liquid, a supersaturated solution of NO in that liquid, or lesser concentrations of NO. The NO may be co-dissolved with another gas that does not react with NO. Gasses that do not react with NO and may be provided in embodiments herein include but are not limited to nitrogen, argon and hydrogen sulfide. The solution may be stored at elevated pressure until immediately prior to application. The liquid may be one in which dissolved oxygen has been removed. The liquid may be one capable of dissolving NO without chemically inactivating NO. The concentration of NO in nitrogen that may be dissolved in the liquid could be any suitable concentration. A suitable concentration may be determined through tests as outlined in the examples, below, or any other test to determine efficacy. The concentration of NO in nitrogen dissolved in the liquid may be any value in a range between any two integer concentrations from 10% to 100%. The concentration of NO in nitrogen may be 10%. The liquid nitric oxide solution may be at atmospheric pressure, but may be at a higher pressure to facilitate aerosolization. The pH of a liquid nitric oxide solution may be neutral. The liquid nitric oxide solution may have an acidic or basic pH. A pH may be selected for reasons including but not limited to antimicrobial efficacy, specific applications, or enhancing shelf life.

The solvent may be any atomizable liquid. The solvent may be any liquid capable of evaporation. The solvent may be selected from water, an alcohol or a combination of water and alcohol. The alcohol may be a combination of different specific alcohols. An alcohol may be selected from ethanol, isopropanol, propanol and methanol or a combination of at least two of ethanol, isopropanol, propanol or methanol. In an embodiment, the solvent is water. In an embodiment, the solvent is deoxygenated water. In an embodiment, the solvent is ethanol.

A liquid nitric oxide solution provided in embodiments herein may contain one or more type of additive. An additive may be a preservative. Preservatives may be but are not limited to butylated hydroyanisole (BHA), butylated hydroxytoluene (BHT), benzoic acid, ascorbic acid, methyl paraben, propyl paraben, tocopherols and mixtures thereof. An additive may be ammonia to alkalinize the solution, or hydrochloric acid to acidify, or other agents that will evaporate and affect the pH. An additive may be at least one antimicrobial agent other than nitric oxide. An additive may be at least one of ethylene glycol or polyethylene glycol. An antimicrobial agent is any substance that kills or inhibits the growth of microorganisms. The microorganisms may bacteria, viruses, molds, slimes, fungi, etc. Antimicrobial agents that may be an additive include but are not limited to halogenated aromatics, chlorinated hydrocarbons, organometallics, metallic salts, organic sulfur compounds, quaternary ammonium compounds, phenolics, triclosan, 3,4,4'-trichlorocarbanilide (triclocarban), 3,4,4'-trifluoromethyl-4,4'-dichlorocarbanilide (cloflucarban), 5-chloro-2-methyl-4-isothiazolin-3-one, iodopropynlbutylcarbamate, 8-hydroxyquinoline, 8-hydroxyquinoline citrate, 8-hydroxyquinoline sulfate, 4-chloro-3,5-xylenol(chloroxylenol), 2-bromo-2-nitropropane-1,3-diol, diazolidinyl urea, butylparaben, ethylparaben, methylparaben, methylchloroisothiazoline, methylisothiazoline, a mixture of 1,3-bis(hydroxymethyl)-5,5-dimethylhydantoin and 3-iodo-2-propynyl butyl carbamate, oxyquinoline, EDTA, tetrasodium EDTA, p-hydroxyl benzoic acid ester, alkyl pyridinum compounds, coco phosphatidyl PG-dimonium chloride, chlorhexidine gluconate, chlorhexidine digluconate, chlorhexidine acetate, chlorhexidine isethionate, chlorhexidine hydrochloride, benzalkonium chloride, benzethonium chloride, polyhexamethylene biguanide, and zinc salt, or mixtures of at least two of the foregoing. In an embodiment, the additive is selected from triclosan and chlorhexidine or a combination thereof. An additive may be an agent that is capable of accelerating or inhibiting evaporation.

The devices and methods herein may cause aerosolization or nebulization of the solution in close proximity to the skin in a manner that directs the solution to the skin while minimizing any chemical reaction of NO with atmospheric oxygen before it reaches the skin. A device herein may enclose the surface to be treated such that the evaporated liquid and the products of chemical reactions between NO and oxygen are prevented from release into the atmosphere, collected and directed through the absorbent material.

In an embodiment, a method herein may include an additional step of producing a liquid nitric oxide solution. Producing a liquid nitric oxide solution may include bubbling NO, an NO/gas mixture, or an NO/nitrogen mixture through ethanol creating a supersaturated solution 12 millimolar NO in ethanol. Bubbling with nitrogen may provide a solution where oxygen is removed. The step of producing may also include sparging with an inert gas such as nitrogen or argon, heating, ultrasonic treatment, vacuum or other comparable method or combination of methods.

A liquid nitric oxide solution may be aerosolized with nitrogen gas and the aerosol may be directed toward the surface to be treated within a device herein. The time for directing the aerosol toward the surface may be several seconds, or 3 seconds.

The liquid nitric oxide solution may be stored under pressure in a canister and released in the direction of the surface to be treated and within a device herein for brief period, in the manner of a can of deodorant or hairspray.

In an embodiment, when the sanitizing is completed, typically after a few seconds, contents of the enclosure may be forced by a fan through the absorbent material as air is drawn into the enclosure.

An indicator may be provided on a device herein when a pre-set system parameter is met to show that a user may remove their hands or the surface that was sanitized. System parameters may be a single volume, a time, or an amount of liquid nitric oxide solution per unit area of the surface inserted.

The liquid nitric oxide solution may be directed to the a surface within a device herein by being forced though a nozzle by a carrier gas such as air or nitrogen, aerosolized or entrained by the carrier gas. Alternatively, the liquid nitric oxide solution may be released from a canister while under pressure. The enclosure may be configured to collect gaseous vapors and the byproducts of NO reactions with oxygen.

Devices and methods herein may be designed for use by persons with no particular skills. Users may be instructed to place their hands up to their wrists inside a device enclosure for a period of time; e.g. 3 seconds, as the solution is sprayed at their skin. An indicator may be associated with the device and configured to show the user that the device is finished, whereupon the user simply removes their hands. Under circumstances where a known contagion such as MRSA is problematic, users may be directed to wear protection; e.g., a standard filter paper mask, to prevent re-contamination of the hands by touching the face.

Any single embodiment herein may be supplemented with one or more element from any one or more other embodiment herein.

EXAMPLES

The following non-limiting examples are provided to illustrate particular embodiments. The embodiments throughout may be supplemented with one or more detail from any one or more example below.

Example 1

Figure 2:
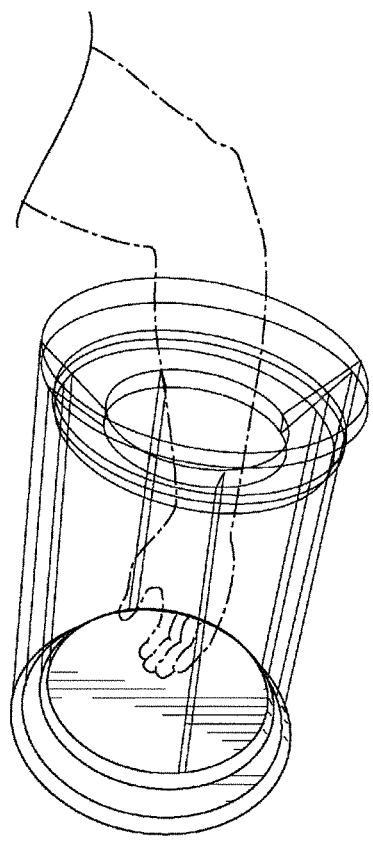
FIG. 2 illustrates an enclosure that may be adapted to be a sanitizing device herein.
Figure 2:
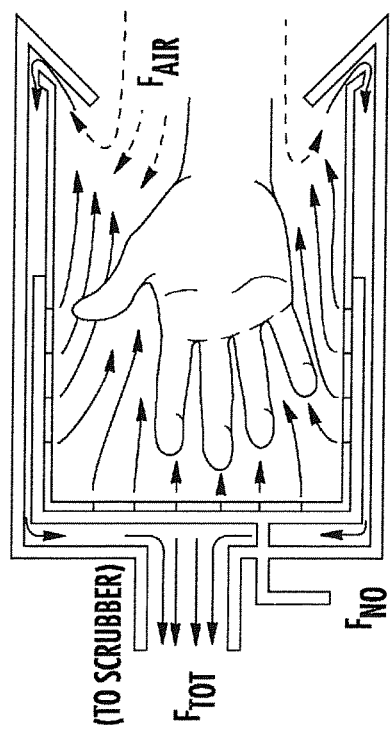

FIG. 2 illustrates an enclosure that may be adapted to serve as a device herein by incorporating one or more of the above described device features in the illustrated enclosure. As illustrated, the enclosure includes channels for directing air flow. Liquid nitric oxide solution may be applied to the user's hand (or any other surface) through one or more dispensers in the walls of the enclosure.

Example 2

Figure 3:
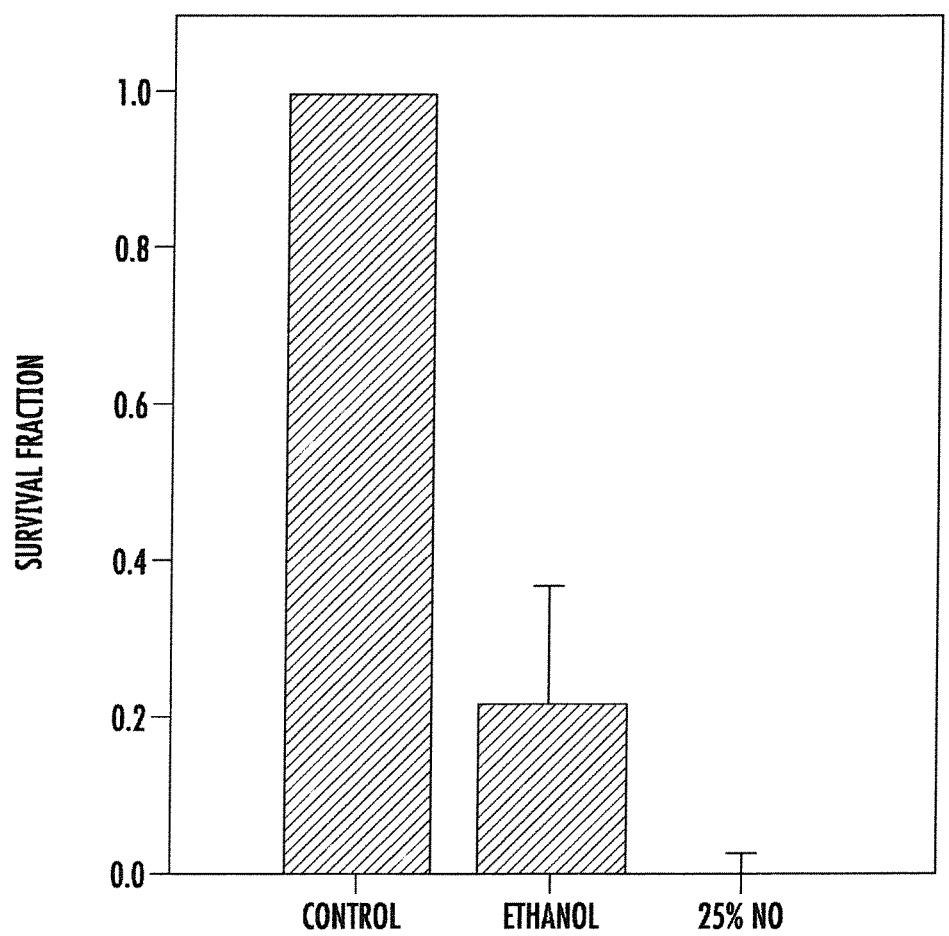
FIG. 3 illustrates results obtained by applying liquid nitric oxide solution. The graph shows the survival of *S. aureus* bacteria on a culture plate following 3 sec. exposures to different conditions. The survival fraction is the fraction of at least 100 colonies that survive the treatment. Control plates were exposed to air for 3 sec. Ethanol plates were exposed to ethanol atomized with nitrogen. 25% NO plates were exposed to ethanol atomized with 25% NO and 75% nitrogen.

Experiments were conducted on agar culture plates to compare nitric oxide concentrations ranging from 0% in nitrogen (the 'ethanol' experiment) to 100% NO. Referring to FIG. 3, results show that agar culture plates are sterilized in less than 3 sec with an exposure of plates with an ethanol solution of 25% NO in nitrogen. In terms of antimicrobial effectiveness, ethanol>isopropanol>water. However, each was effective and may be a solvent in an effective device or method. However, none of these liquids are effective by themselves; i.e. when atomized with nitrogen. NO dramatically increases the antimicrobial activity of the atomized liquid. Regardless of the liquid used, the mist to which these plates are exposed feels cool, and the liquid component evaporated in less than a second. The chemical properties and toxicities of NO make it unlikely that any NO would penetrate the skin, and that any toxicities would ensue from repeated brief exposures.

Further Embodiments

The following list of embodiments is provided to list non-limiting embodiments and is not to be construed as limiting on any of the above embodiments or examples thereof, or the claims.

Embodiments

1. A device for rapidly sanitizing a surface comprising: an enclosure having an opening adapted to insert a surface and an interior; a liquid nitric oxide solution applicator; and an absorbent material, wherein the liquid nitric oxide solution applicator is in fluid communication with the interior of the enclosure and is adapted to apply liquid nitric oxide solution onto the surface to be treated when the surface is positioned within the enclosure.

2. The device of embodiment 1 further comprising at least one of a container or scrubber configured to receive at least one of nitric oxide and reaction products with nitric oxide.

3. The device of any one or more of the preceding embodiments further comprising a containment system for moving at least one of nitric oxide and reaction products with nitric oxide toward at least one of the absorbent material, into the container, and into the scrubber.

4. The device of any one or more of the preceding embodiments further comprising a system to deliver an oxygen-free inert gas atmosphere to the interior of the enclosure and/or maintain an oxygen-free inert gas atmosphere in the interior of the enclosure.

5. The device of any one or more of the preceding embodiments, wherein the system includes a source of nitrogen, argon, carbon dioxide, another chemically unreactive gas, or combinations thereof, wherein the source is in fluid communication with the interior of the enclosure.

6. The device of any one or more of the preceding embodiments further comprising a tracking element.

7. A method of rapidly sanitizing a surface comprising:

providing a device for rapidly sanitizing a surface, the device including an enclosure having an opening adapted to insert a surface and an interior; a liquid nitric oxide solution applicator; and an absorbent material, wherein the liquid nitric oxide solution applicator is in fluid communication with the interior of the enclosure and a liquid nitric oxide source, and is adapted to apply the liquid nitric oxide solution onto the surface;

inserting a surface to be treated into the device; and applying the liquid nitric oxide solution to the surface to be treated.

8. The method of embodiment 7, wherein the device further includes at least one of a container or scrubber configured to receive at least one of nitric oxide and reaction products with nitric oxide.

9. The method of any one or more of embodiments 7-8, wherein the device further includes a containment system for moving at least one of nitric oxide and reaction products with nitric oxide toward at least one of the absorbent material, into the container, and into the scrubber.

10. The method of any one or more of embodiments 7-9, wherein the device further includes a system to deliver an oxygen-free inert gas atmosphere to the interior of the enclosure and/or maintain an oxygen-free inert gas atmosphere in the interior of the enclosure, the method further comprising at least one of delivering an oxygen-free inert gas atmosphere to the interior of the enclosure or maintaining an oxygen-free inert gas atmosphere in the interior of the enclosure.

11. The method of any one or more of embodiments 7-10, wherein the system includes a source of nitrogen, argon, carbon dioxide, another chemically unreactive gas, or combinations thereof, the source is in fluid communication with the interior of the enclosure, and the step of delivering or maintaining includes injecting the nitrogen, argon, carbon dioxide, another chemically unreactive gas, or combinations thereof into the interior of the enclosure.

12. The method of any one or more of embodiments 7-11, wherein the liquid nitric oxide solution includes a liquid solvent selected from the group consisting of water, alcohol, and a mixture of water and alcohol.

13. The method of any one or more of embodiments 7-12, wherein the liquid solvent is water.

14. The method of any one or more of embodiments 7-13, wherein the step of applying the liquid nitric oxide solution to the surface includes activating the liquid nitric oxide solution applicator.

15. The method of any one or more of embodiments 7-14 further comprising activating the containment system.

16. The method of any one or more of embodiments 7-15, wherein rapidly sanitizing includes killing an infectious agent.

17. The method of any one or more of embodiments 7-16, wherein the surface to be treated is on a body part.

18. The method of embodiment 17, wherein the body part is a human body part.

19. The method of embodiments 17 or 18, wherein the body part is a human hand.

20. The method of any one or more of embodiments 7-16, wherein the surface to be treated is on an in-animate object.

21. The method of any one or more of embodiments 7-16, wherein the surface to be treated is on a personal item, a household item, a workplace item, a medical facility item, a school item, a daycare item, a church item, a manufacturing item, a food packaging item, a drug manufacturing item, a food or food ingredient, or a drug or drug component.

22. The method of any one or more of embodiments 7-21, wherein the device further includes a tracking element.

23. The method of embodiment 22, wherein the method further includes tracking at least one of users implementing the method or the surface to be treated.

24. A method of rapidly sanitizing a surface comprising:
inserting a surface to be treated into a device for rapidly sanitizing a surface, the device including an enclosure having an opening adapted to insert a surface and an interior; a liquid nitric oxide solution applicator; and an absorbant material, wherein the liquid nitric oxide solution applicator is in fluid communication with the interior of the enclosure and a liquid nitric oxide source, and is adapted to apply the liquid nitric oxide solution onto the surface; and
applying the liquid nitric oxide solution to the surface to be treated.

25. The method of embodiment 24, wherein the device further includes at least one of a container or scrubber configured to receive at least one of nitric oxide and reaction products with nitric oxide.

26. The method of any one or more of embodiments 24-25, wherein the device further includes a containment system for moving at least one of nitric oxide and reaction products with nitric oxide toward at least one of the absorbent material, into the container, and into the scrubber.

27. The method of any one or more of embodiments 24-26, wherein the device further includes a system to deliver an oxygen-free inert gas atmosphere to the interior of the enclosure and/or maintain an oxygen-free inert gas atmosphere in the interior of the enclosure, the method further comprising at least one of delivering an oxygen-free inert gas atmosphere to the interior of the enclosure or maintaining an oxygen-free inert gas atmosphere in the interior of the enclosure.

28. The method of any one or more of embodiments 24-27, wherein the system includes a source of nitrogen, argon, carbon dioxide, another chemically unreactive gas, or combinations thereof, the source is in fluid communication with the interior of the enclosure, and the step of delivering or maintaining includes injecting the nitrogen, argon, carbon dioxide, another chemically unreactive gas, or combinations thereof into the interior of the enclosure.

29. The method of any one or more of embodiments 24-28, wherein the liquid nitric oxide solution includes a liquid solvent selected from the group consisting of water, alcohol, and a mixture of water and alcohol.

30. The method of any one or more of embodiments 24-29, wherein the liquid solvent is water.

31. The method of any one or more of embodiments 24-30, wherein the step of applying the liquid nitric oxide solution to the surface includes activating the liquid nitric oxide solution applicator.

32. The method of any one or more of embodiments 24-31 further comprising activating the containment system.

33. The method of any one or more of embodiments 24-32, wherein rapidly sanitizing includes killing an infectious agent.

34. The method of any one or more of embodiments 24-33, wherein the surface to be treated is on a body part.

35. The method of embodiment 34, wherein the body part is a human body part.

36. The method of embodiments 34 or 35, wherein the body part is a human hand.

37. The method of any one or more of embodiments 24-33, wherein the surface to be treated is on an in-animate object.

38. The method of any one or more of embodiments 24-33, wherein the surface to be treated is on a personal item, a household item, a workplace item, a medical facility item, a school item, a daycare item, a church item, a manufacturing item, a food packaging item, a drug manufacturing item, a food or food ingredient, or a drug or drug component.

39. The method of any one or more of embodiments 24-33, wherein the device further includes a tracking element.

40. The method of embodiment 39, wherein the method further includes tracking the surface to be treated.

41. A system comprising the device of any one of embodiments 1-6 and at least one of a computer or network of computers, the computer or network of computers includes a computer-readable medium and processor executable instructions stored in the computer-readable medium, wherein the processor executable instructions include instructions for implementing the method of any one or more of embodiments 7-40.

It is understood, therefore, that this invention is not limited to the particular embodiments disclosed, but is intended to cover all modifications which are within the spirit and scope of the invention as defined by the appended claims and/or the above description.

What is claimed is:

1. A device for rapidly sanitizing a surface of an object comprising:
   an enclosure having an opening adapted to insert the object therethrough, an interior portion of the enclosure adapted to receive the surface from the enclosure, and having an absorbent material; and
   a liquid nitric oxide solution applicator comprising a liquid conduit, wherein the liquid conduit is connected to an atomizer or a nebulizer to dispense a liquid nitric oxide solution having an antimicrobial activity;
   wherein the liquid nitric oxide solution applicator is in fluid communication with the interior portion of the enclosure and is adapted to apply the liquid nitric oxide solution onto the surface in a manner sufficient to rapidly sanitize the surface.

2. The device of claim 1 further comprising at least one of a container or scrubber configured to receive at least one of nitric oxide and reaction products with nitric oxide.

3. The device of claim 2 further comprising a containment system adapted to direct at least one of nitric oxide and reaction products with nitric oxide toward at least one of the absorbent material, into the container, and into the scrubber.

4. The device of claim 1 further comprising a system to deliver an oxygen-free inert gas atmosphere to the interior of the enclosure and/or maintain an oxygen-free inert gas atmosphere in the interior of the enclosure.

5. The device of claim 4, wherein the system includes a source of nitrogen, argon, carbon dioxide, another chemically unreactive gas, or combinations thereof, wherein the source is in fluid communication with the interior of the enclosure.

6. The device of any one of the preceding claims further comprising a tracking element.

7. A system comprising the device of claim 1 and at least one of a computer or network of computers, the computer or network of computers including a computer-readable medium and processor executable instructions stored in the computer-readable medium, wherein the processor executable instructions include instructions for rapidly sanitizing a surface comprising:
   applying the liquid nitric oxide solution to a surface to be treated upon insertion the surface to be treated into the device.

8. The device of claim 1, wherein the enclosure encloses the surface such that at least one of nitric oxide and reaction products with nitric oxide are prevented from release into the atmosphere.

9. The device of claim 1, wherein the device is adapted to force at least one of nitric oxide and reaction products with nitric oxide through the absorbent material and draw air into the interior.

10. The device of claim 1, wherein the liquid nitric oxide solution is provided via the atomizer or nebulizer by a carrier gas.

11. The device of claim 10, wherein the carrier gas is air or nitrogen.

12. The device of claim 10, wherein the liquid nitric oxide solution is aerosolized.

13. The device of claim 10, wherein the atomizer or nebulizer is adapted to direct the liquid nitric oxide solution to the surface.

* * * * *